United States Patent [19]

Alberghini et al.

[11] 4,327,574

[45] May 4, 1982

[54] NON-DESTRUCTIVE DISSOLVED GAS VOLUME TESTING METHOD

[75] Inventors: Alfred C. Alberghini, Dunwoody; Dennis C. Donalson, Marietta, both of Ga.

[73] Assignee: Sewell Plastics, Inc., Atlanta, Ga.

[21] Appl. No.: 171,041

[22] Filed: Jul. 22, 1980

[51] Int. Cl.³ .............................................. G01N 7/00
[52] U.S. Cl. ........................................... 73/19; 73/52
[58] Field of Search .......................... 73/19, 23, 37, 52

[56] References Cited

U.S. PATENT DOCUMENTS

| | | | |
|---|---|---|---|
| 2,736,191 | 2/1956 | Bockelmann et al. | 73/19 |
| 2,737,803 | 3/1956 | Doudera, Jr. et al. | 73/37 |
| 3,958,448 | 5/1976 | Willis et al. | 73/37 |
| 4,208,903 | 6/1980 | Hopper et al. | 73/52 |

Primary Examiner—Stephen A. Kreitman
Attorney, Agent, or Firm—Jenkins, Coffey, Hyland, Badger & Conard

[57] ABSTRACT

A method for measuring the amount of a gas, such as carbon dioxide, dissolved in a liquid in a sealed thin-walled container without piercing the container or breaking the seal of the container. This is accomplished by deforming the thin-walled container by exerting a known force thereon, measuring the resulting deflection of the container, and measuring the ambient temperature of the liquid. By reference to a pre-calibrated chart, one can then find the amount of gas dissolved in the liquid at the known temperature and calculated pressure.

5 Claims, 2 Drawing Figures

NON-DESTRUCTIVE DISSOLVED GAS VOLUME TESTING METHOD

BACKGROUND OF THE INVENTION

The ability to measure the amount of carbon dioxide dissolved in a liquid is important for quality control in the carbonated beverage industry. Up to now, the only available methods for making this determination have involved the piercing of a sealed container. For example, U.S. Pat. No. 3,958,448, issued to Willis et al, discloses a pressure test method and apparatus in which a needle pierces the container. It has been common in the past to determine the volume of carbon dioxide in a bottle of a carbonated drink by putting a pressure gauge in communication with the bottle contents via a hollow needle inserted into the bottle.

These methods destroy the seal between the contents of the container and the outside atmosphere, thus rendering the bottle useless for further tests at a later time. Consequently, to test the shelf life of a bottled carbonated beverage is difficult and expensive since the same bottle or bottles cannot be tested repeatedly to determine the carbon dioxide content of the beverage as a function of time. This determination has become increasingly important since the advent of thin-walled plastic containers which are considerably more pervious to gases than the glass containers which have been used for carbonated beverages in the past.

It is an object of the invention to provide a method for determining the amount of a gas dissolved in a liquid in a thin-walled container without destroying the container by piercing it. It is a further object of the invention to provide a method for determining the amount of gas dissolved in a liquid in a thin-walled container to a high degree of accuracy. Such a method will make the determination of shelf-life of a carbonated liquid inexpensive, less difficult, and more accurate.

Throughout the description of this invention, reference is made to carbon dioxide dissolved in a liquid in a bottle. That the invention can be applied to other gases dissolved in liquids in other types of thin-walled containers will, however, be apparent to the reader.

DESCRIPTION OF THE INVENTION

At a constant temperature and constant amount of gas, the product of pressure times volume is a constant. Thus, if one adds pressure to the gas, a corresponding change in volume will occur. If the gas is contained in a flexible container, pressure can be added by exerting a force on the outside of the container sufficient to deform the container. For a given amount of force, the deformation of the container will be a function of the pressure of the gas since for a given change in pressure, the change in volume will be a function of the pressure.

If a known amount of force is applied to a thin-walled container by a plunger travelling in a straight line, the distance travelled by the plunger can be used as a measure of the deformation, or deflection, of the container. Then, for any given deflection at a constant temperature, and a given amount of applied force, the corresponding gas pressure, or the amount of gas dissolved in the liquid, can be read off a pre-calibrated chart or graph.

Figure 1:
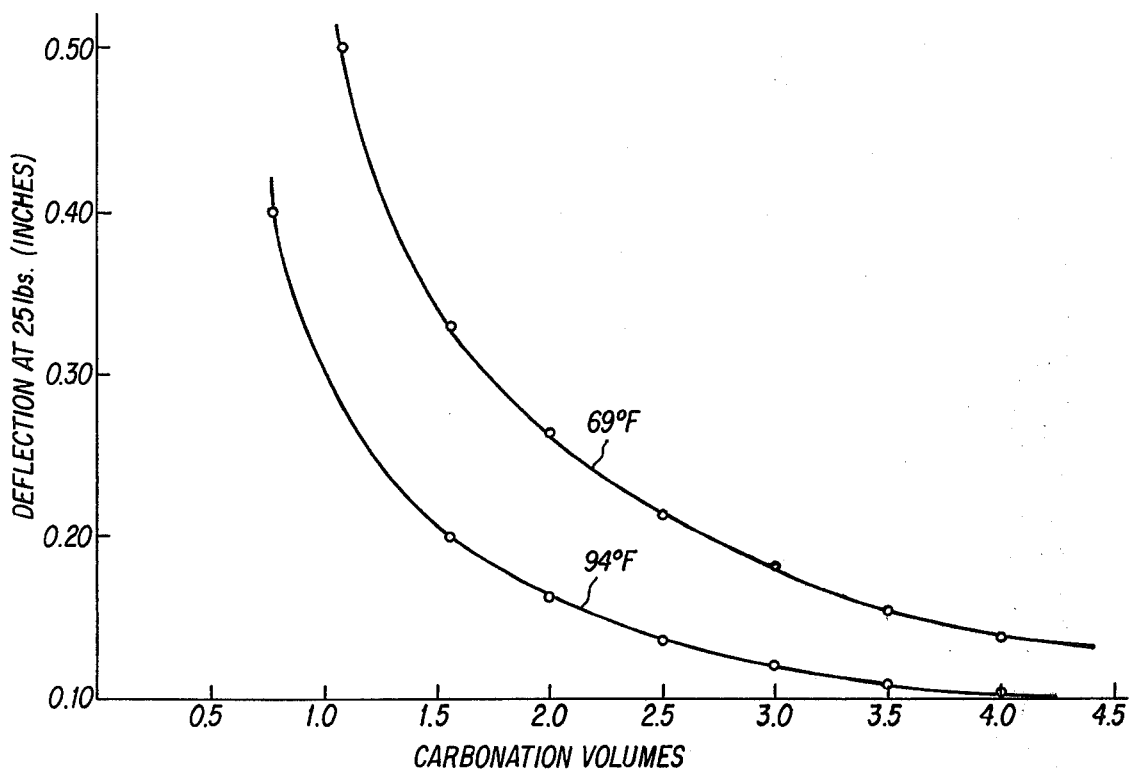
FIG. 1 is a graph of amount of gas dissolved in a liquid versus deflection of the container at various temperatures.

Experiment has verified that this can be done. A graph of deflection from a constant applied force versus amount of gas dissolved in a liquid at a constant temperature shows a well defined curve. FIG. 1 shows such a graph.

To make a pre-calibrated graph as shown in FIG. 1, one applies a known force on the outside of the thin-walled container and notes the amount of deflection of the container. This can be done by measuring the distance travelled by a force-exerting plunger moving in a straight line perpendicular to the container. Then, one can use conventional methods to determine the amount of gas dissolved in the liquid, like using a Zahmand Nagel pressure tester. At constant temperatures, and constant applied force, a plot of deflection vs. amount of dissolved gas will yield curves as shown in FIG. 1.

Once such a graph is obtained, it can be used to determine the amount of dissolved gas corresponding to any amount of deflection.

The duration of time over which the force is applied to the outside of the bottle must be short enough so that the amount of carbon dioxide in the head space does not change appreciably because of more carbon dioxide being dissolved into the liquid in response to the increase in pressure. To keep the change in amount of $CO_2$ in the head space negligible, it is most desirable that the duration of the application of the force be on a time scale of less than one minute.

Error can be minimized by placing the bottle and the experimental apparatus in a liquid bath or other temperature-controlled environment, thereby facilitating the maintenance of a constant temperature throughout the experiment.

Another possible source of error in the pressure determination is the resistance to the applied force exerted by the bottle itself. The amount of error involved here, however, is not significant if the applied force is very large in comparison to the resistance of the bottle wall itself.

During the carbonation process, a small amount of air enters a beverage bottle along with the carbon dioxide. However, the amount of air in the head space need not be accounted for since its presence leads only to a slight error in that determination of the amount of carbon dioxide in the liquid. Many studies relating to this error have been done by others, for example W. P. Heath, and the factors are reasonably well known. Where shelf life testing is done according to this invention, the error due to the presence of air in the head space would largely be self-compensating.

Figure 2:
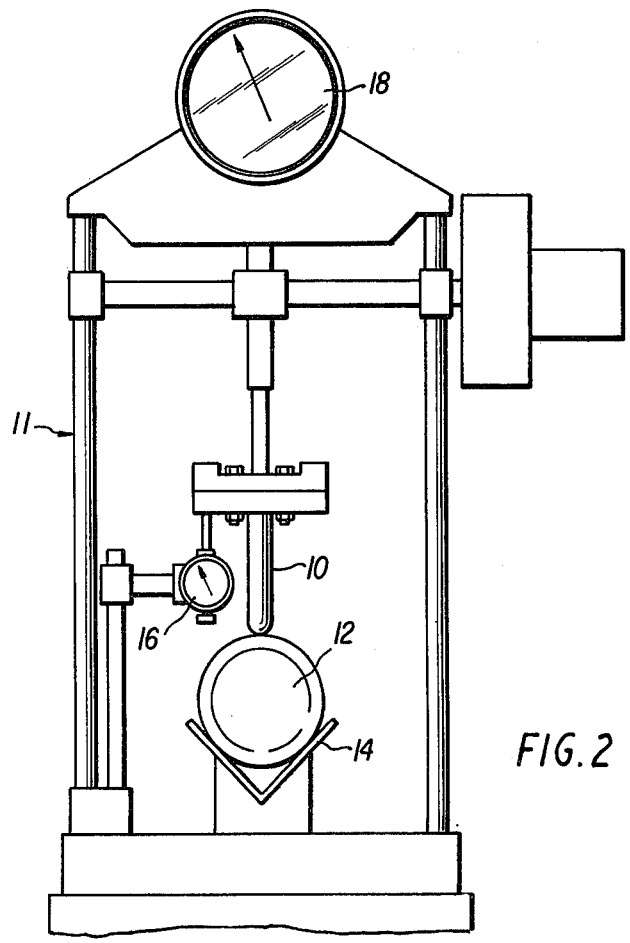
FIG. 2 is a view of an apparatus for carrying out the method of the invention.

Referring to FIG. 2, the apparatus for carrying out the method includes a means to exert a measured amount of force on the containers such as a small plunger 10 supported by a frame 11 which can exert a measured amount of force on the side of the bottle 12 resting on a support 14 at the bottom of the frame 11. Typically, the plunger 10 will have a cross-sectional area of about one inch and will be capable of exerting forces in the range of 25 to 100 pounds. It is to be understood that these parameters may be varied, depending upon the need of the user.

In a preferred embodiment, the plunger 10 may travel downward to contact a bottle 12 resting on its side, although it may travel sideways to contact a bottle standing upright.

The apparatus also includes an indicator 16 to show how far the plunger has deflected the bottle side, and means to indicate how much force is being applied 18. A modified top end loader can be used to carry out the method of the invention when a bottle support is added to its structure.

To maintain a constant temperature while performing a test on a bottle, a controlled temperature cabinet can be mounted on the frame 11 to enclose the bottle 12 and plunger 10.

What is claimed is:

1. A method for determining the amount of gas dissolved in a liquid contained in a sealed, thin-walled container including a head space containing a quantity of undissolved gas, the container and its contents being maintained at a constant temperature, the method comprising the steps of:

supplying a known force on a surface of the container for a period of time insufficient to cause any gas in the head space to dissolve into the liquid, the known force being sufficient to deform the container, and measuring the amount of deformation of the container.

2. The method of claim 1 wherein the known force is applied normal to a thin-walled portion of the container.

3. The method of claim 1 wherein the known force is applied normal to the container surface.

4. The method of claim 3 wherein the amount of deformation is determined by measuring the maximum distance over which the container surface is deflected in the direction of the known force.

5. The method of claim 3 wherein the known force is applied in a vertical direction.

* * * * *